US005744474A

United States Patent [19]
Thor

[11] Patent Number: 5,744,474
[45] Date of Patent: Apr. 28, 1998

[54] TREATMENT OF INCONTINENCE

[75] Inventor: Karl B. Thor, Carmel, Ind.

[73] Assignee: Eli Lilly and Company, Indianapolis, Ind.

[21] Appl. No.: 425,703

[22] Filed: Apr. 20, 1995

Related U.S. Application Data

[63] Continuation of Ser. No. 158,121, Nov. 24, 1993, abandoned.

[51] Int. Cl.$^6$ .................. A61K 31/135; A61K 31/34; A61K 31/38; A61K 31/44
[52] U.S. Cl. .................. 514/357; 514/365; 514/438; 514/471; 514/649; 514/651
[58] Field of Search .................. 514/357, 365, 514/438, 471, 649, 651

[56] References Cited

U.S. PATENT DOCUMENTS

| | | | |
|---|---|---|---|
| 4,314,081 | 2/1982 | Molloy et al. | 564/347 |
| 4,761,501 | 8/1988 | Husbands et al. | 564/167 |
| 4,956,388 | 9/1990 | Robertson et al. | 514/651 |
| 5,023,269 | 6/1991 | Robertson et al. | 514/438 |
| 5,192,751 | 3/1993 | Thor | 514/82 |
| 5,250,571 | 10/1993 | Fuller et al. | 514/651 |
| 5,281,624 | 1/1994 | Gehlert et al. | 514/651 |

FOREIGN PATENT DOCUMENTS

| | | |
|---|---|---|
| 052492 | 5/1982 | European Pat. Off. . |
| 288188 | 10/1988 | European Pat. Off. . |
| 367040 | 5/1990 | European Pat. Off. . |
| 501705 | 2/1992 | European Pat. Off. . |

OTHER PUBLICATIONS

Springer, et al., *J. Urology*, 152, 515–519 (1994).
Mesaros, et al., *J. Am. Acad. Child Adolesc. Psychiatry*, 32, 877–878 (1993).
Ambrosini, et al., *J. Am. Acad. Child Adolesc. Psychiatry*, 32, 483–493 (1993).
Michael R. Trimble, *J. Clin. Psychiatry*, 51, 51–54 (1990).
G. Beaumont, *J. Int. Med. Res.*, 1, 435–437 (1973).
Wong, et al., *Neuropsychopharmacology*, 8, 23–33 (1993).
Foreman, M.M., and McNulty, A.M., *Life Sciences*, 53, 193–200 (1993).
Mesaros, J.D., *J. Am. Acad. Child Adolesc. Psychiatry*, 32, 877–878 (1993).
Wong et al., *J. Pharmacology and Experimental Therapeutics*, 222(1), 61–65 (1982).
*The Merck Manual*, pp. 1639–1641, published by Merck & Co., Inc., Rahway, N.J. (1987).
Rushton, *J. Pediatrics*, 114(2), 691–696 (1989).
Shaffer et al., *Neuropharm.*, 18, 33 (1979).
Lipshultz et al., *Invest. Urology*, 11, 182 (1973).
Khanna et al., *Urology*, 6, 48 (1975).
Zerbe et al., *J. Pharmacol. Ex. Ther.*, 232(1), 139–143 (1985).
Bertilsson et al., *Clin. Pharmacol. Ther.*, 40(3), 261–267 (1986).
Cohen et al., *J. Pharmacol. Exp. Ther.*, 248(3), 1063–1068 (1989).
Goodman et al., *Pharmacological Basis of Therapeutics* 7th ed., Macmillan Pub. Co., New York, pp. 85 and 422 (1985).
Thor et al., *Dev. Brain Res.*, 54, 35–42 (1990).
Kiminao Mizukawa, *Anat. Anz.*, 147, 125–144 (1980).
Espey, *Soc. for Neuroscience Abst.*, 17, 1003 (1991).
Rajaofetra, *J. Comp. Neurol.*, 318, 1–17 (1992).
Kojima et al., *Cell Tissue Res.*, 229, 23–36 (1983).
Rasmussen, et al., *Synapse*, 5, 325–332 (1990).
Kojima et al., *Cell Tissue Res.*, 226, 477–491 (1982).
Ryall, *Brain Res.*, 37, 345–47 (1972).
Roberts et al., *Br. J. Pharmacol.*, 95, 437–48 (1988).
White et al., *Brain Res.*, 188, 119–27 (1980).
McMahon et al., *Brain Res.*, 234, 237–249 (1982).
Kojima et al., *Histochemistry*, 81, 237–41 (1984).
Maggi et al., *J. Pharmacol. Exp. Ther.*, 248, 278–85 (1989).
Espey et al., *Eur. J. Pharmacol.*, 221, 167–70 (1992).
White et al., *Prog. Brain Res.*, 88, 343–50 (1991).
Birder et al., *Soc. for Neuroscience Abst.*, 19, 51.15 (1993).
Bux et al., *Ann. Hematol.*, 63, 249–252 (1991).

*Primary Examiner*—Richard L. Raymond
*Attorney, Agent, or Firm*—Robert D. Titus; David E. Boone

[57] ABSTRACT

Urinary incontinence in humans is treated by administration of venlafaxine or a compound chosen from a series of aryloxy propanamines.

19 Claims, 5 Drawing Sheets

LY53857 (0.1 mg/kg i.v.)

CMG after LY53857

FIGURE 5a
Control (CMG)

Hypogastric Nerve Activity

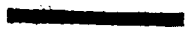
External Urethral EMG

Bladder Pressure

FIGURE 5b
Duloxetine (3.0 mg/kg)

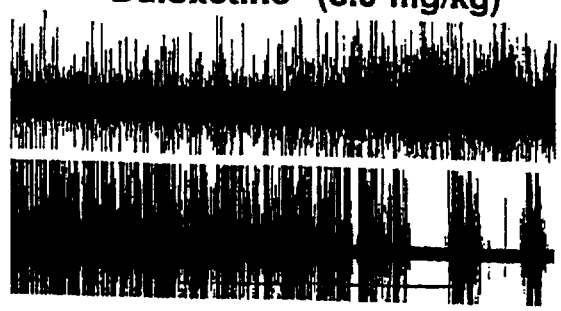
Hypogastric Nerve Activity / External Urethral EMG

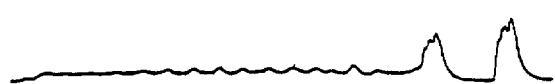
Bladder Pressure

FIGURE 5c
LY53857 (3.0 mg/kg)

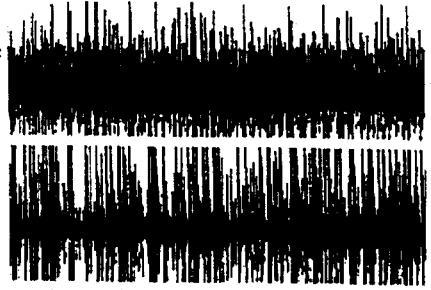
Hypogastric Nerve Activity / External Urethral EMG

FIGURE 5d
Prazocin (1.0 mg/kg)

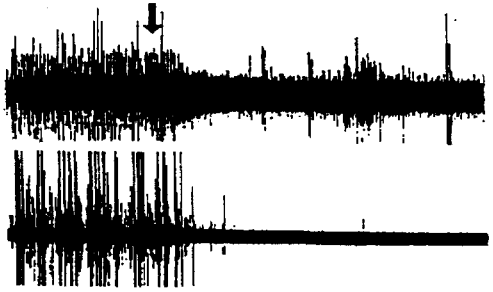
Hypogastric Nerve Activity / External Urethral EMG

FIGURE 5e  CMG post Prazocin

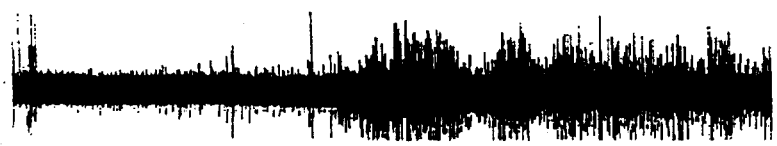
Hypogastric Nerve Activity

External Urethral EMG

Bladder Pressure

TREATMENT OF INCONTINENCE

This application is a continuation of application Ser. No. 08/158,121, filed on Nov. 24, 1993, now abandoned.

FIELD OF THE INVENTION

This invention belongs to the fields of pharmaceutical chemistry and pharmacological treatment, and provides a new method of treating incontinence in humans, making use of a series of 3-aryloxypropanamines, particularly duloxetine.

BACKGROUND OF THE INVENTION

Urinary incontinence is a common condition, and often is so severe as to constitute an embarrassing and even disabling difficulty. It is a frequent cause of elderly people's confinement to nursing homes and other protected environments. While it is more common among women than among men, at all ages, it afflicts significant numbers of both sexes. It is well known that many children past the usual age of toilet-training suffer from nocturnal enuresis, and less frequently from daytime urinary incontinence, and it is also well known that the elderly are quite likely to develop urinary incontinence as they grow older. However, some studies have reported daily incontinence among as many as 17% of young, apparently healthy, women.

Thus, it is clear that reliable and safe methods of treating urinary incontinence are seriously needed. The need is not, at present, adequately met.

Urinary incontinence is a manifestation of the failure of control of the muscles of the urinary sphincter and of the bladder. Those muscles are in balance, when the system is operating properly. The urinary sphincter should be sufficiently strong to hold back the pressure exerted by the muscles of the bladder, except when the subject consciously relaxes the sphincter in order to urinate.

Incontinence results when the pressure within the bladder is too great, as a result of excessive force exerted by the muscles of the bladder, or when the urinary sphincter is too weak to hold back the normal intra-bladder pressure. Incontinence is broadly classified as urge incontinence (caused by excessive intra-bladder pressure), and stress incontinence (caused by a weak urethral sphincter). Patients often are seen with both urge and stress incontinence, a condition which is called mixed incontinence.

Urinary incontinence, appearing in different types of patients, has a number of different causes or apparent causes, including Parkinsonism, multiple sclerosis, cerebral vascular system damage, cerebral arteriosclerosis, lesions of the central nervous system, and infections of the bladder. Instability of the muscles of the bladder or urethra can have many causes, and interstitial cystitis can result in instability of the bladder detrusor muscles and result in a particularly painful and unpleasant variety of urge incontinence.

Neurological disorders, including Parkinsonism, Alzheimer's disease, and multiple sclerosis, often result in urge incontinence, occurring through hyperactivity of the bladder muscles. Urinary incontinence is an early symptom of Parkinsonism, and in fact, is often made worse by anti-Parkinson's drugs.

It is well known that children frequently have nocturnal incontinence. It has been reported that nocturnal incontinence occurs in 30% of 4-year-old children, and in 10% of 6-year-old children. This condition is a variety of urge incontinence and is a well-known source of emotional unrest in both children and their parents.

Many elderly people suffer from incontinence, which may result from many causes and include both stress and urge incontinence, as well as mixed incontinence resulting from a complex of causes. Urge incontinence is most common in the elderly, usually caused by abnormal nervous or muscular responses of the bladder. Stress incontinence, relatively rare in elderly men, but more common in elderly women, can result from surgery, decreased muscle tone and anatomical changes in the pelvic organs, deterioration of the urethra, and deterioration in the neuromuscular response of the urethra. The diseases of the elderly, especially Alzheimer's disease, also frequently result in incontinence.

Thus, it is clear that urinary incontinence is one of the major diseases of today. It is believed to afflict approximately 12 million people in the United States alone, and to occur in from 15 to 30% of the population over the age of 60. Its treatment at present is quite unsatisfactory.

Probably most patients are not treated at all, but use diapers, and other aids, mostly remaining close to home in a state of embarrassment and isolation. Some types of incontinence can be improved by surgery, at great cost and some risk. The improvement is usually temporary with the average patient receiving 2.3 surgeries in her lifetime. A few drugs are in use, including particularly imipramine and other anti-cholinergic and anti-spasmotic agents. Benzodiazepine anti-depressants, ephedrine and phenylpropanolamine are used to some extent.

All of the drugs now used for urinary incontinence have the disadvantage of possessing numerous pharmacological activities, and therefore causing unwanted responses in the patients. The anti-cholinergic effects of the benzodiazepines and of imipramine are particularly significant and are likely to produce side effects which require withdrawal of the medication, or result in noncompliance by the patient.

Thus, it is clear that pharmaceuticals effective for the treatment of urinary incontinence, and free from undesired side effects, are badly needed. The present invention provides such pharmaceuticals.

SUMMARY OF THE INVENTION

The present invention provides a method of treating urinary incontinence in a human in need of such treatment, comprising administering to such human an effective incontinence-reducing dose of venlafaxine or a compound of the formula $$R^1-CHCH_2CH_2NR^2R^3 \qquad I$$
$$\underset{Ar}{\overset{|}{O}}$$

wherein: $R^1$ is $C_5-C_7$ cycloalkyl, thienyl, halothienyl, $(C_1-C_4$ alkyl)thienyl, furanyl, pyridyl or thiazolyl;

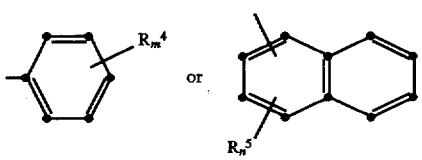

each of $R^2$ and $R^3$ independently is hydrogen or methyl;
each $R^4$ independently is halo, $C_1-C_4$ alkyl, $C_1-C_3$ alkoxy or trifluoromethyl;
each $R^5$ independently is halo, $C_1-C_4$ alkyl or trifluoromethyl;
m is 0, 1 or 2;

n is 0 or 1; or a pharmaceutically acceptable acid addition salt thereof.

The invention also provides a pharmaceutical product for the treatment of urinary incontinence in a human, which product comprises venlafaxine or a compound of formula I, in the form of a pharmaceutical formulation additionally comprising a pharmaceutically acceptable excipient, in combination with packaging material suitable for the pharmaceutical formulation, said packaging material including instructions for the use of the pharmaceutical formulation to treat urinary incontinence.

DESCRIPTION OF THE FIGURES

FIG. 5—The effects of duloxetine on hypogastric nerve activity, external urethral EMG and bladder pressure, compared with LY53857 and prazocin.

DETAILED DESCRIPTION OF THE INVENTION

Figure 1:
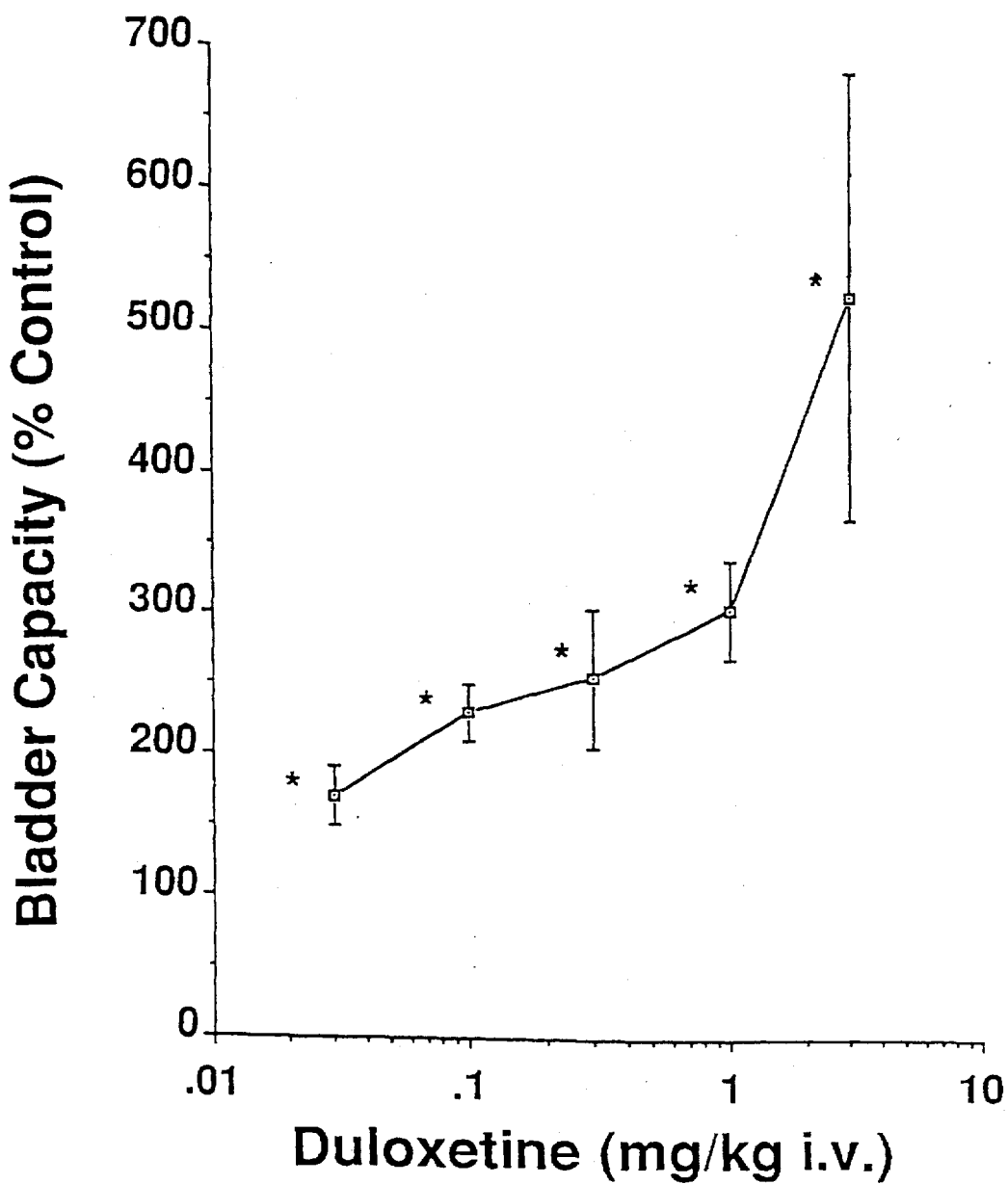
FIG. 1—The effect of administration of duloxetine on bladder capacity.
Figure 2:
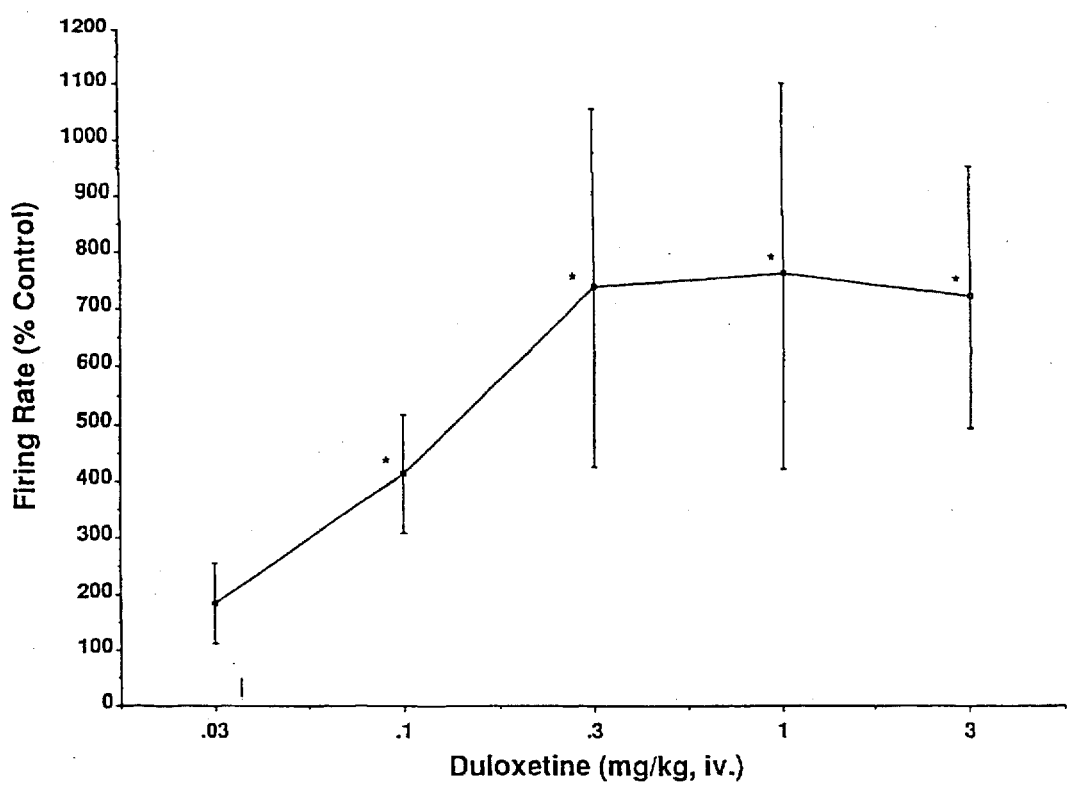
FIG. 2—The effect of duloxetine on the activity of external urethral sphincter muscles, measured by EMG activity.
Figures 3A, 3B:
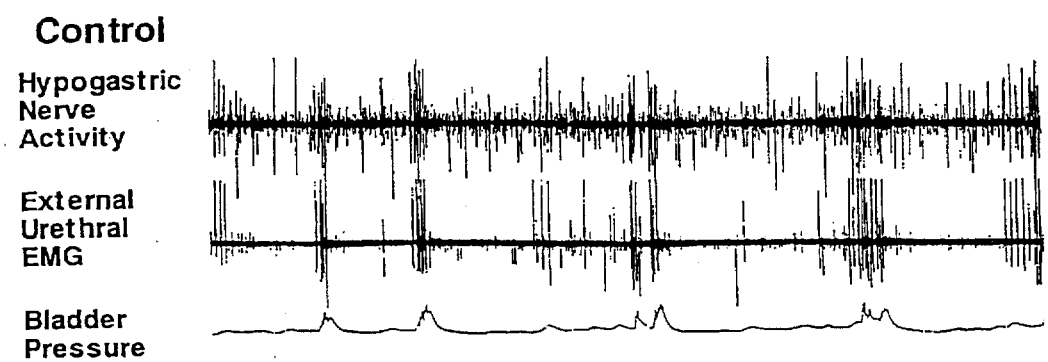
FIG. 3—The effects of duloxetine on hypogastric nerve activity, external urethral EMG and bladder pressure.

In this document, all temperatures will be indicated in degrees Celsius, and all indications of percentage, ratio, concentration and like will be expressed in weight measurements unless otherwise indicated.

The Compounds

The compounds useful in the present invention are selective inhibitors of the reuptake of both serotonin and norepinephrine, and have substantially no other pharmacological effects. That is to say, any other pharmacological effects which the compounds may have occur only at concentrations or dosages at least 10, and usually 100 times larger than the effective concentrations or dosages at which the compounds inhibit the uptake of serotonin and norepinephrine. Thus, the compounds are substantially unable to cause undesired side effects in the patients to whom the compounds are administered.

Venlafaxine is a known compound in the literature, and its method of synthesis and its activity as an inhibitor of serotonin and norepinephrine uptake are taught by U.S. Pat. No. 4,761,501. Venlafaxine is identified as compound A in that document, which is incorporated by reference here. At column 9 of that patent, it is stated that compound A has no muscarinic anti-cholinergic actions.

The compounds of formula I have been taught by U.S. Pat. No. 4,956,388, which is also incorporated by reference here. The most preferred compound of formula I is duloxetine, (+)-N-methyl-3-(1-naphthalenyloxy)-3-(2-thienyl)propanamine, usually administered as the hydrochloride salt. Duloxetine is prepared in the form of the oxalate in Example 2 of that patent, which shows its high potency in the inhibition of serotonin and norepinephrine uptake at column 16.

Since the compounds of formula I are completely taught in U.S. Pat. No. 4,956,388, the reader may learn the methods of synthesis and the complete description of the compounds from that document. Certain of the compounds are preferred for use in the presently disclosed invention, however, and groups of those preferred compounds will be mentioned here. It will be understood that preferred groups described below may be combined at will to describe other, more limited subgroups, which are also particularly preferred in the practice of the present invention.

a) $R^1$ is thienyl;
b) $R^1$ is thienyl, halothienyl, or $(C_1-C_4$ alkyl)thienyl;
c) $R^1$ is $C_5-C_7$ cycloalkyl;
d) $R^1$ is furanyl, pyridyl or thiazolyl;
e) Ar is phenyl or substituted phenyl;
f) Ar is napthyl or substituted napthyl;
g) Ar is unsubstituted phenyl or unsubstituted napthyl;
h) $R^2$ is methyl and $R^3$ is hydrogen;
i) $R^2$ and $R^3$ are both methyl.

The reader will understand that the compounds of formula I, as well as venlafaxine, possess an asymmetric carbon atom, and that they accordingly exist in the form of individual stereoisomers, as well as the racemic mixture. When the stereoisomeric form of a compound is not indicated in this document, it will be understood that both of the possible isomeric forms, as well as the racemate, are intended. When an individual stereoisomer is indicated, as in the case of duloxetine, the isomeric form will be stated as part of the name.

For example, the following specific compounds illustrate the compounds of formula I which are contemplated in the scope of the present invention.

N-Methyl-3-(1-naphthalenyloxy)-3-(3-thienyl)propanamine phosphate (+)-N-Methyl-3-(2-naphthalenyloxy)-3-(cyclohexyl) propanamine citrate (+)-N,N-Dimethyl-3-(4-chloro-1-naphthalenyloxy)-3-(3-furanyl)propanamine hydrochloride N-Methyl-3-(5-methyl-2-naphthalenyloxy)-3-(2-thiazolyl) propanamine hydrobromide N-Methyl-3-[3-(trifluoromethyl)-1-naphthalenyloxy]-3(3-methyl-2-thienyl)propanamine oxalate (−)-N-Methyl-3-(6-iodo-1-naphthalenyloxy)-3-(4-pyridyl) propanamine maleate N,N-Dimethyl-3-(1-naphthalenyloxy)-3-(cycloheptyl) propanamine formate (−)-N,N-Dimethyl-3-(2-naphthalenyloxy)-3-(2-pyridyl) propanamine (+)-N-Methyl-3-(1-naphthalenyloxy)-3-(2-furanyl)propanamine sulfate (+)-N-Methyl-3-(4-methyl-1-naphthalenyloxy)-3-(4-thiazolyl)propanamine oxalate N-Methyl-3-(2-naphthalenyloxy)-3-(2-thienyl)propanamine hydrochloride (−)-N,N-Dimethyl-3-(6-iodo-2-naphthalenyloxy)-3-(4-bromo-3-thienyl)propanamine malonate (−)-N,N-Dimethyl-3-(1-naphthalenyloxy)-3-(3-pyridyl) propanamine hydroiodide N,N-Dimethyl-3-(4-methyl-2-naphthalenyloxy)-3-(3-furanyl)propanamine maleate (+)-N-Methyl-3-(2-naphthalenyloxy)-3-(cyclohexyl) propanamine caprate (−)-N-Methyl-3-(6-n-propyl-1-naphthalenyloxy)-3-(3-isopropyl-2-thienyl)propanamine citrate (+)-N,N-Dimethyl-3-(2-methyl-1-naphthalenyloxy)-3-(4-thiazolyl)propanamine monohydrogen phosphate 3-(1-Naphthalenyloxy)-3-(5-ethyl-3-thienyl)propanamine succinate 3-[3-(Trifluoromethyl)-1-naphthalenyloxy]-3-(pyridyl) propanamine acetate (−)-N-Methyl-3-(6-methyl-1-naphthalenyloxy)-3-(4chloro-2-thienyl)propanamine tartrate 3-(2-Naphthalenyloxy)-3-(cyclopentyl)propanamine (−)-N-Methyl-3-(4-n-butyl-1-naphthalenyloxy)-3-(3-furanyl)propanamine methanesulfonate (+)-3-(2-Chloro-1-naphthalenyloxy)-3-(5-thiazolyl)propanamine oxalate (+)-N-Methyl-3-(1-naphthalenyloxy)-3-(3-furanyl)propanamine tartrate N,N-Dimethyl-3-(phenoxy)-3-(2-furanyl)propanamine oxalate N,N-Dimethyl-3-[4-(trifluoromethyl)phenoxyl]-3-(cyclohexyl)propanamine hydrochloride N-Methyl-3-(4-methylphenoxy)-3-(4-chloro-2-thienyl)propanamine propionate (−)-N-Methyl-3-(phenoxy)-3-(3-pyridyl)propanamine oxalate 3-[2-Chloro-4-(trifluoromethyl)phenoxy]-3-(2-thienyl)propanamine (+)-N,N-Dimethyl-3-(3-methoxyphenoxy)-3-(3-bromo-2-thienyl)propanamine citrate N-Methyl-3-(4-bromophenoxy)-3-(4-thiazolyl)propanamine maleate (−)-N,N-Dimethyl-3-(2-ethylphenoxy)-3-(5-methyl-3-thienyl)propanamine N-Methyl-3-(2-bromophenoxy)-3-(3-thienyl)propanamine succinate (−)-N-Methyl-3-(2,6-dimethylphenoxy)-3-(3-methyl-2-thienyl)propanamine acetate 3-[3-(Trifluoromethyl)phenoxy]-3-(3-furanyl)propanamine oxalate (−)-N-Methyl-3-(2,5-dichlorophenoxy)-3-(cyclopentyl)propanamine 3-[4-(Trifluoromethyl)phenoxy]-3-(2-thiazolyl) propanamine (+)-N-Methyl-3-(phenoxy)-3-(5-methyl-2-thienyl)propanamine citrate (+)-3-(4-(Methoxyphenoxy)-3-(4-pyridyl)propanamine hydrochloride N,N-Dimethyl-3-(3-methyl-5-bromophenoxy)-3-(3-thienyl)propanamine N-Methyl-3-(3-n-propylphenoxy)-3-(2-thienyl)propanamine hydrochloride (+)-N-Methyl-3-(phenoxy)-3-(3-thienyl)propanamine phosphate (−)-N-Methyl-3-(4-methoxyphenoxy)-3-(cycloheptyl)propanamine citrate 3-(2-(Chlorophenoxy)-3-(5-thiazolyl)propanamine propionate 3-[2-Chloro-4-(trifluoromethyl)phenoxy]-3-(3-thienyl)propanamine oxalate 3-(Phenoxy)-3-(4-methyl-2-thienyl)propanamine (+)-N,N-Dimethyl-3-(4-ethylphenoxy)-3-(3-pyridyl)propanamine maleate (−)-N,N-Dimethyl-3-[4-(trifluoromethyl)phenoxy]-3-(2-pyridyl)propanamine A particularly preferred synthesis of the most preferred compound, duloxetine, will be set out below to assure that the reader is fully informed.

PREPARATION 1

(S)-(−)-N,N-dimethyl-3-hydroxy-3-(2-thienyl)-propanamine

A mixture of 8.18 g of 2-acetylthiophene, 6.66 g of dimethylamine hydrochloride, 2.9 g of paraformaldahyde and 0.31 g of concentrated hydrochloric acid in 20 ml of isopropanol was heated to reflux and stirred for 6 hours. The mixture was then cooled to 0° and stirred for one hour more. The slurry was then filtered, and the solid was washed with cold ethanol. The washed solid was dried for 16 hours at 50° to obtain 12.5 g of 2-thienyl 2-dimethylaminoethyl ketone hydrochloride, as a white solid. A 12.0 g portion of that intermediate product was stirred in 40 ml of ethanol at ambient temperature, and the pH of the solution was raised to 11–12 by slow addition of sodium hydroxide. A 1.03 g portion of sodium borohydride was added, and the mixture was stirred at ambient temperature for 4 hours. Then 7.5 ml of acetone was added, and the mixture was stirred for 20 minutes more. The mixture was then concentrated by evaporation to a white slurry, and 120 ml of methyl t-butyl ether was added. The mixture was acidified to pH 1–1.5 by addition of concentrated hydrochloric acid, and the solution was stirred for ten minutes. The pH was then made basic to pH 12 by slow addition of sodium hydroxide.

The layers were then separated, the aqueous phase was extracted with 30 ml of methyl t-butyl ether, and the organic phases were combined and washed once with 50 ml of water. The organic phase was concentrated by evaporation to 118 ml, and was heated to 50°.

In a separate vessel, (S)-(+)-mandelic acid, 4.18 g, was dissolved in 12 ml of ethanol at 50°, and the mandelic acid solution was added slowly to the previous solution. The resulting slurry was then heated to reflux and stirred for 45 minutes. It was then cooled to ambient temperature, stirred for one hour, and filtered, and the solid was washed with methyl t-butyl ether. The solid was then dried under vacuum at 50° to obtain 7.29 g of the mandelic acid salt of the desired product, which is isolated as the free amine by dissolution in water, basification with sodium hydroxide solution, extraction into an organic solvent, and evaporation to remove the solvent.

PREPARATION 2

(S)-(+)-N,N-dimethyl-3-(1-naphthalenyloxy)-3-(2-thienyl)propanamine, phosphoric acid salt A 13.5 g portion of (S)-(−)-N,N-dimethyl-3-hydroxy-3-(2-thienyl)propanamine was dissolved in 80 ml of dimethylsulfoxide at 25°. To the solution was slowly added 3 g of sodium hydride as a 60% dispersion in mineral oil, with vigorous stirring. After 15 minutes of stirring, 1.17 g of potassium benzoate was added and stirring was continued at approximately constant temperature for another 15 minutes. Then, 12.8 g of 1-fluoronaphthalene was slowly added to the reaction mixture, and after the addition was complete, the mixture was heated and was stirred for 2.5 hours at 60°–65°. The mixture was then poured slowly into 190 ml of cold water and the pH was adjusted to 4.8 by addition of acetic acid. The temperature of the mixture was brought to 25°, and 75 ml of hexane was added and stirring was continued for 10 minutes. The layers were then separated and the aqueous phase was stirred again with 75 ml of hexane and the phases separated. The pH of the aqueous phase was adjusted to 10.2 by addition of aqueous sodium hydroxide, and 75 ml of ethyl acetate was added. That mixture was stirred for 15 minutes at 25°, and the 2-phase mixture was vacuum filtered through a pad of filter aid. The phases of the filtrate were allowed to separate, and the aqueous phase was extracted with 75 ml of ethyl acetate. The extract was combined with the previous ethyl acetate layer, and that mixture was washed with 100 ml of water. The organic layer was stirred at 25°, and to it was added, dropwise, 7 g of 85% phosphoric acid. After the addition was complete, the mixture was stirred for 20 minutes more and was then cooled to 0° and stirred for 1 hour at that temperature. The slurry was then filtered and the solids washed three times with 20 ml portions of cold ethyl acetate. The solid was dried at 60° to afford 24.19 g of the title compound as a white solid, 98.1% potency, adjusted yield 79.6%, 91% EE.

Assay Methodology

The product was analyzed by high performance liquid chromatography, using a Spectra Physics SP 8800 instrument equipped with a SP 4400 integrator and a Spectroflow 757 detector, set at 230 nm, at a sensitivity of 0.5 absorption units, 1 second filter rise time. The column was a Dupont Zorbax RX $C_{8,\ 4.6}$ mm×25 cm. The eluant was 70% acetonitrile, 30% 0.01M phosphate buffer at pH 6, flow rate of 1.0 ml/minute, injection volume 20 microliters. The samples were prepared by diluting 0.1 to 0.3 g of reaction mixture or extract to 50 ml with 1:1 acetonitrile:water. The product peak elutes at 13–17 minutes; starting material at 6–8 minutes; fluoronaphthalene at 5–6 minutes; dimethylsulfoxide at 2–3 minutes; and potassium benzoate at 2–2.5 minutes.

When a chiral assay was to be done, the same equipment was set at 280 nm and a sensitivity of 0.1 absorption unit, and a Chiralcel OD column was used. The eluant for chiral assays was 2% isopropanol, 0.2% diethylamine, and 97.8% hexane. The same injection and flow settings were used. The samples were prepared by diluting 0.1–0.3 g of reaction mixture or extract to 5 ml with dichloromethane, washing the mixture with about 5 ml of water, and drying the organic phase over sodium sulfate. The resulting solution was filtered and diluted to 25 ml with eluant. The desired enantiomer elutes at 5–5.5 minutes, the undesired enantiomer at 6–6.5 minutes and fluoronaphthalene at 3–4 minutes.

PREPARATION 3

(+)-N-methyl-3-(1-naphthalenyloxy)-3-(2-thienyl) propanamine hydrochloride

Five g of the product of Preparation 2 was stirred in a mixture of 40 ml of toluene and 40 ml of water at 40°, and 2.5 ml of 30% ammonium hydroxide solution was added. The mixture was stirred for 10 minutes at constant temperature and the layers were separated. The organic phase was washed with water, dried with magnesium sulfate and filtered. The filtrate was concentrated to half volume under vacuum and was heated to 55°. Then 0.16 g of diisopropylethylamine was added, followed by the dropwise addition of 2.39 g of phenyl chloroformate. The mixture was stirred at 55° for 1.25 hours, and 50 ml of 1% sodium bicarbonate solution was added. The mixture was stirred for ten minutes at 40°–50°, and the phases were separated. The organic phase was washed twice with 0.5N hydrochloric acid, and then washed with 1% sodium bicarbonate solution. The washed organic phase was divided in half, and one aliquot was evaporated under vacuum and 26 ml of dimethylsulfoxide was added to the residue. The mixture was heated to 45°, and 1 g of sodium hydroxide and 6 ml of water was added dropwise. The basic mixture was stirred for 18 hours at 50°, diluted with 17 ml of water, and acidified to pH 5.0–5.5 by addition of acetic acid. Then 20 ml of hexane was added, the mixture was stirred for ten minutes, and the phases separated. The aqueous phase was made basic to pH 10.5 by addition of 50% aqueous sodium hydroxide, and 17 ml of ethyl acetate was added. After stirring for 10 minutes, the phases were separated, and the aqueous layer was extracted with another 17 ml of ethyl acetate. The combined organic extracts were washed with water and concentrated to 10 ml under vacuum. 0.46 g of concentrated hydrochloric acid was added to the residue, and then a seed crystal and an additional 10 ml of ethyl acetate was added. The mixture was stirred for 30 minutes more, and the solution was concentrated to 10 ml under vacuum. The residue was stirred for 1 hour at ambient temperature and 1 hour at 0° to produce a slurry, which was filtered. The solid was washed with chilled ethyl acetate to obtain 1.32 g of the desired product, which was duloxetine as a white solid of potency 99.8%.

The Disease and Its Treatment

The method of the present invention is used to treat and control urinary incontinence of either or both the stress and urge types, in patients of any age in need of such treatment. The cause of the stress, urge or mixed urinary incontinence is not critical to the benefit of the present invention. Incontinence caused by deterioration of the central nervous system, the peripheral nervous system, the muscles of the bladder or urethra, and infections of bladder or urethra are all effectively treated by the present method.

The types of urinary incontinence which have been called or caused by detrusor instability, interstitial cystitis, and nocturnal enuresis of either the primary or secondary type, are included within either stress or urge incontinence and are effectively treated by the present method. Still further, urinary incontinence brought about by pelvic surgery, anatomical changes in the geometry of the bladder and urethra, urethral deterioration as a result of cessation of estrogen production, and bladder hyperactivity are all effectively treated.

It will be demonstrated by the biological testing examples which follow that the method of the present invention has the astonishing ability to increase the effective volume of the bladder, and simultaneously to increase the contractility and nervous system control of the muscles which manage the urethra. Accordingly, it is clear that the present invention controls both urge incontinence, by increasing the effective volume of the bladder and decreasing involuntary muscular activity around the bladder, and stress incontinence, by increasing voluntary control of the urethral sphincter and improving tone of the urethral musculature.

Accordingly, the method of the present invention is carried out simply by administering an incontinence-decreasing dose of a compound of formula I, or venlafaxine, to a patient in need of that treatment. The effective dose is variable, and will always be determined by the physician in charge of the patient. Further, it should be noted that it may be necessary to adjust the dose of a compound when it is administered in the form of a salt such as, e.g., a laurate, the salt-forming moiety of which has an appreciable molecular weight. In general, however, the range of effective doses is from about 1 to about 50 mg/day per patient. A preferred rate range is from about 5 to about 20 mg/kg day. Of course, it is often practical to administer the daily dose of a pharmaceutical compound in portions, at various hours of the day.

The route of administration of the compounds of this invention is not critical. The compounds are absorbed from the alimentary tract, and so it is usually preferred to administer them orally, for convenience. They may be administered, however, by any pharmaceutically acceptable route if desired in a given instance.

The compounds of this invention are usually administered as pharmaceutical compositions which, in combination with appropriate instructions for administering the composition in order to provide treatment for incontinence, are important and novel embodiments of the invention. The patents which teach the compounds also discuss the pharmaceutical compositions. All of the usual types of pharmaceutical compositions may be used, including tablets, chewable tablets, capsules, solutions, parenteral solutions, suspensions, suppositories, and troches. Compositions are preferably formulated to contain a daily dose, or a convenient fraction of a daily dose, in a dosage unit which may be a single solid entity such as a tablet, or may be convenient volume of a liquid or semi-solid. The activity of the compounds does not depend on the compositions in which they are administered or on the concentration of the compositions, and thus, the compositions are chosen and formulated solely for reasons of convenience and economy in use. Any of the compounds may be readily formulated as tablets, capsules and the like; it is obviously preferable to prepare solutions, such as those for injection, from water-soluble salts of the compounds.

In general all of the compositions are prepared according to methods usual in pharmaceutical chemistry. A group of typical formulae of compositions will be mentioned below, but the principles of such formulations are so well known that no detailed discussion will be provided.

Formulation 1

Hard gelatin capsules are prepared using the following ingredients

|  | Quantity (mg/capsule) |
|---|---|
| Duloxetine hydrochloride | 5 |
| Starch, dried | 445 |
| Magnesium stearate | 10 |
| Total | 460 mg |

Formulation 2

A tablet is prepared using the ingredients below:

|  | Quantity (mg/capsule) |
|---|---|
| (+)-N-methyl-3-(1-naphthalenyloxy)-3-(2-thiazolyl)propanamine oxalate | 10 |
| Cellulose, microcrystalline | 640 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| N-methyl-3-[4-(trifluoromethyl)phenoxy]-3-(2-furanyl)propanamine maleate | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 20 mg of active ingredient, are made as follows:

| N,N-dimethyl-3-(4-methyl-1-naphthalenyloxy)-3-(2-thienyl)propanamine phosphate | 20 mg |
|---|---|
| Starch | 85 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

| (−)-N,N-dimethyl-3-(1-naphthalenyloxy)-3-(cyclohexyl)propanamine oxalate | 5 mg |
|---|---|
| Starch | 134 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatine capsules in 200 mg quantities.

Formulation 6

Suppositories, each containing 10 mg of active ingredient, are made as follows:

| (+)-N-methyl-3-(1-naphthalenyloxy)-3-(3-pyridyl)propanamine hydrochloride | 10 mg |
|---|---|
| Saturated fatty acid glycerides | 2,000 mg |
| Total | 2,010 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 10 mg of active ingredient per 5 ml dose, are made as follows:

| | |
|---|---|
| N,N-dimethyl-3-(4-methoxyphenoxy)-3-(2-thienyl)propanamine citrate | 10 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the soidum carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| | |
|---|---|
| (−)-N,N-dimethyl-3-(4-chlorophenoxy)-3-(4-chloro-2-thienyl)-propanamine succinate | 100 mg |
| Isotonic saline | 1,000 ml |

The solution of the above ingredients generally is administered intravenously to a subject at a rate of 1 ml per minute.

The amount of active ingredient incorporated into the formulation of this invention is not critical; the concentration should only be in a range sufficient to permit ready administration of the formulation in an amount which will deliver the desired amount of active ingredient.

Example of Therapeutic Effect

Tests showing the powerful effect of the preferred compound in the treatment of both stress and urge incontinence are presented here. It will be understood that the results shown here are representative of the virtues of the invention in its full scope.

Seven female cats (2.5–3.5 kg) were anesthetized with alpha-chloralose (50–75 mg/kg i.v.) following induction with isoflurane. A cannula was inserted into the trachea. One catheter was inserted into the carotid artery for measuring systemic blood pressure, and another was placed in the radial vein for injecting drugs.

Cystometrograms (CMGs) were conducted via a catheter (PE90) inserted through the dome of the bladder, which was used for both saline infusion and for recording of intravesical pressure. EMG electrodes were placed in the peri-urethral striated muscle. CMG infusion rates ranged from 0.3 ml/min to 1 ml/min to achieve a micturition contraction within 10 minutes of starting infusion. Micturition contractions were accompanied by release of bladder contents, which was measured by collecting the fluid in a cylinder attached to a force transducer. After reaching micturition threshold, saline infusion was continued and resulted in rhythmic bladder contractions and releases being maintained. During this time of rhythmic bladder activity, duloxetine was administered and its effects on rhythmic contractions noted. Five minutes after duloxetine administration, the bladder was emptied and another CMG performed.

In 3 of the 7 cats, efferent input to the bladder was activated by electrically stimulating the pelvic nerve with square-wave pulses of 0.05 msec, 10 Hz, sub-maximal intensity (0.5–8 V) and the resultant pressure increase was recorded.

Duloxetine was dissolved in 14% ethanol (10 mg/ml) and diluted with saline to allow appropriate dose injection in a volume of 0.1–0.3 ml/kg administered intravenously. Prazosin, an $\alpha_1$ adrenergic receptor antagonist, (Sigma, St. Louis, Mo.) was dissolved in dilute HCL to a concentration of 1 mg/ml and diluted with saline to a concentration of 0.1 mg/ml. LY53857, 6-methyl-1-(1-methylethyl)ergoline-8-carboxylic acid, 2-hydroxy-1-methylpropyl ester (Z)-2-butenedioate, a $5HT_2$ receptor antagonist, was dissolved in saline with gentle warming.

Duloxetine produced dose-dependent increases in bladder capacity in all 7 cats, to about five times the capacity seen under control conditions (FIGS. 1, 2, 4, and 5). Doses of 10 mg/kg (n=3) completely abolished micturition contractions (infusions were stopped after reaching the tonus limb of the CMG profile, which indicates that the elastic limits of the bladder are being reached). The increase in bladder capacity was not accompanied by changes in the amplitude or duration of the contractions upon reaching micturition threshold volumes (FIGS. 2, 3, 4, and 5). Similarly, there was no increase in the residual volume of the bladder (calculated by subtracting the amount released from the amount infused). Duloxetine also reduced the frequency of micturition contractions (20% of control frequency at 3 mg/kg) and proportionately increased the amount of urine released with each contraction (5 fold at 3 mg/kg). The effects of duloxetine on bladder activity were seen within 4 minutes of administration. No effects of duloxetine were seen on bladder contractions evoked by maximal electrical stimulation of efferent fibers in the pelvic nerve. LY53857 (3 mg/kg, i.v.), alone or in combination with prazosin (300 µg/kg, i.v.), did not reverse duloxetine's effects on bladder activity.

Under control conditions (FIGS. 3 and 5), there was very little peri-urethral muscle EMG activity during the filling phase of the CMG.

Within 4 minutes of duloxetine administration there was a dose-dependent increase in peri-urethral muscle EMG activity recorded during rhythmic bladder contractions produced by continuous infusion. During the filling phase of the CMG, activity increased (FIGS. 2, 3, 4, and 5) to 8 times control levels at a dose of 0.3 mg/kg with larger doses producing no greater effect on average. Activity was also increased about 8 fold during the period immediately following the micturition contraction. In the 4 cats that originally showed peri-urethral activity during micturition contractions, the intermittent periods of quiescence (i.e. bursting patterns) were maintained. In those 3 cats that displayed no urethral EMG activity during bladder contractions under control conditions, marked inhibition of peri-urethral sphincter activity was observed during bladder contractions. In other words, despite the increase in peri-urethral EMG activity during the filling phase of the CMG, synergy between the bladder contraction and sphincter relaxation was maintained in these latter 3 cats (FIG. 5).

Figure 4A:
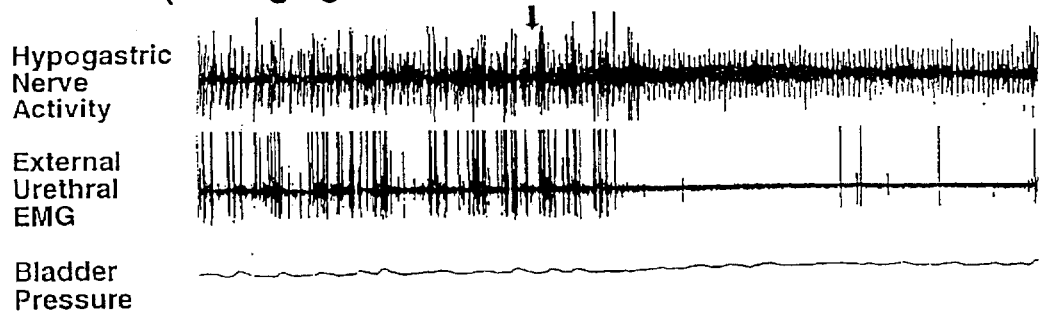
FIG. 4—The effects of LY53857, for comparison with FIG. 3; LY53857 was administered at the time indicated by the arrow.
Figure 4B:

In 4 of 6 cats, the increase in peri-urethral sphincter EMG activity was completely abolished by LY53857 (100–300 µg/kg, i.v.), a 5HT2 receptor antagonist (FIG. 4). In the other 2 of 6 cats, LY53857 (100 µg/kg, i.v.) decreased peri-urethral sphincter EMG activity to 50% and 33% of the duloxetine-induced levels of activity, respectively, and larger doses (to 3 mg/kg, i.v.) produced no further decrease (FIG. 5). subsequent administration of prazosin (100 µg/kg, i.v.) did abolish peri-urethral sphincter EMG activity (FIG. 5).

The results show that duloxetine increases bladder capacity and peri-urethral (i.e. sphincteric) striated muscle activity.

Concurrent with increases in peri-urethral EMG activity, duloxetine also inhibited bladder activity, increasing the bladder volume necessary to evoke micturition. Although capacity was increased, there was no effect on the amplitude or duration of the contractions once they were initiated. This indicates that duloxetine increases the sensory threshold necessary to elicit a micturition contraction, but it was not effecting motor response of the contraction once the elevated micturition threshold was passed. This finding, and more importantly the finding that there was no effect of duloxetine on bladder contractions evoked by stimulation of peripheral efferent axons in the pelvic nerve, indicates that the inhibitory effects of duloxetine on bladder activity were mediated centrally. It is also important to note that although duloxetine increased urethral sphincter activity, the synergistic interaction between bladder contraction and sphincter activity was maintained.

The increase in bladder capacity by duloxetine indicates utility for the treatment of urge incontinence, while the increase in tonic peri-urethral sphincter EMG activity indicates utility for stress incontinence. Since there is currently no single effective treatment for both types of urinary incontinence, such a compound provides a substantial medical advancement for these patients. Since duloxetine had no effect on the magnitude of the bladder contraction once it had reached micturition threshold, micturition occurred as efficiently as it had before drug treatment. This is important in light of the fact that current incontinence medicines (primarily anticholinergics) cause decreased efficiency of micturition and increases in residual urine due to compromise of bladder contractile force.

I claim:

1. A method of treating urinary incontinence in a human in need of such treatment, comprising administering to such human an effective incontinence-reducing dose of venlafaxine or a compound of the formula $$R^1\text{—}\underset{\underset{Ar}{\overset{|}{O}}}{\overset{|}{C}}HCH_2CH_2NR^2R^3 \qquad I$$

wherein: $R^1$ is $C_5$–$C_7$ cycloalkyl, thienyl, halothienyl, ($C_1$–$C_4$ alkyl)thienyl, furanyl, pyridyl or thiazolyl;

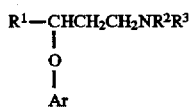 or 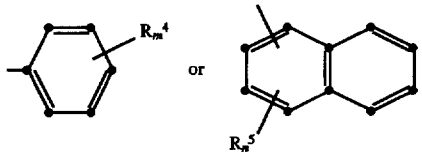

each of $R^2$ and $R^3$ independently is hydrogen or methyl;

each $R^4$ independently is halo, $C_1$–$C_4$ alkyl, $C_1$–$C_3$ alkoxy or trifluoromethyl;

each $R^5$ independently is halo, $C_1$–$C_4$ alkyl or trifluoromethyl;

m is 0, 1 or 2;

n is 0 or 1; or a pharmaceutically acceptable acid addition salt thereof.

2. A method of claim 1 wherein the incontinence is urge incontinence.

3. A method of claim 1 wherein the incontinence is stress incontinence.

4. A method of claim 1 wherein the compound is venlafaxine.

5. A method of claim 1 wherein the compound is a compound of formula I as defined in claim 1.

6. A method of claim 1 wherein the incontinence is both stress and urge incontinence.

7. A method of claim 5 wherein the incontinence is both stress and urge incontinence.

8. A method of claim 5 wherein the incontinence is urge incontinence.

9. A method of claim 5 wherein the incontinence is stress incontinence.

10. A method of claim 5 wherein the compound is a compound wherein $R^1$ is thienyl, halothienyl, or ($C_1$–$C_4$ alkyl)-thienyl.

11. A method of claim 5 wherein the compound is a compound wherein Ar is naphthyl or substituted naphthyl.

12. A method of claim 10 wherein the compound is a compound wherein Ar is naphthyl or substituted naphthyl.

13. A method of claim 5 wherein the compound is a compound wherein Ar is unsubstituted phenyl or unsubstituted naphthyl.

14. A method of claim 10 wherein the compound is a compound wherein Ar is unsubstituted phenyl or unsubstituted naphthyl.

15. A method of claim 5 wherein the compound is duloxetine or a pharmaceutically acceptable salt thereof.

16. A method of claim 7 wherein the compound is duloxetine or a pharmaceutically acceptable salt thereof.

17. A method of claim 8 wherein the compound is duloxetine or a pharmaceutically acceptable salt thereof.

18. A method of claim 9 wherein the compound is duloxetine or a pharmaceutically acceptable salt thereof.

19. A method of claim 15 wherein the incontinence is nocturnal incontinence.

* * * * *

UNITED STATES PATENT AND TRADEMARK OFFICE
CERTIFICATE OF CORRECTION

PATENT NO. : 5,744,474
DATED : Apr. 28, 1998
INVENTOR(S) : Karl B. Thor

It is certified that error appears in the above-identified patent and that said Letters Patent is hereby corrected as shown below:

Column 13, line 50, delete " 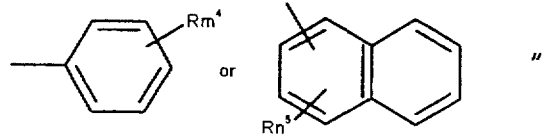 "

and insert therefor -- Ar is 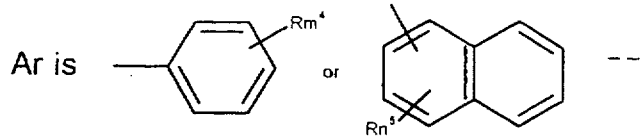 --

Signed and Sealed this

Seventh Day of September, 1999

Attest:

Q. TODD DICKINSON

Attesting Officer *Acting Commissioner of Patents and Trademarks*